United States Patent
Cappiello et al.

(12) 
(10) Patent No.: US 6,913,611 B2
(45) Date of Patent: Jul. 5, 2005

(54) RECTOSIGMOID MANIPULATOR APPARATUS

(76) Inventors: Gerard Cappiello, 1965 Lynwood Ct., Dunedin, FL (US) 34698-2845; Mimi Cappiello, 1965 Lynwood Ct., Dunedin, FL (US) 34698-2845

( * ) Notice: Subject to any disclaimer, the term of this patent is extended or adjusted under 35 U.S.C. 154(b) by 111 days.

(21) Appl. No.: 10/308,679

(22) Filed: Dec. 3, 2002

(65) Prior Publication Data

US 2004/0106943 A1 Jun. 3, 2004

(51) Int. Cl.$^7$ ............................................. A61M 29/00
(52) U.S. Cl. ................................. 606/192; 604/97.01
(58) Field of Search ............................ 606/159, 167, 606/170, 191, 192, 164.02, 164.03, 164.12; 600/156, 207; 623/1.11; 128/898

(56) References Cited

U.S. PATENT DOCUMENTS

| | | | |
|---|---|---|---|
| 3,721,229 A | | 3/1973 | Panzer |
| 4,434,789 A | | 3/1984 | Kumar |
| 4,447,227 A | | 5/1984 | Kotsanis |
| 5,464,409 A | | 11/1995 | Mohajer |
| 5,496,345 A | * | 3/1996 | Kieturakis et al. .......... 606/192 |
| 5,746,749 A | | 5/1998 | Willard |
| 5,814,060 A | * | 9/1998 | Fogarty et al. ............. 606/192 |
| 5,836,913 A | | 11/1998 | Orth et al. |
| 5,925,058 A | * | 7/1999 | Smith et al. ................ 606/190 |
| 5,935,098 A | | 8/1999 | Blaisdell et al. |
| 5,989,230 A | | 11/1999 | Frassica |
| 6,176,849 B1 | | 1/2001 | Yabg et al. |
| 6,264,604 B1 | * | 7/2001 | Kieturakis et al. .......... 600/207 |
| 6,306,154 B1 | | 10/2001 | Hudson et al. |
| 6,379,334 B1 | | 4/2002 | Frassica |

* cited by examiner

Primary Examiner—Julian W. Woo
Assistant Examiner—Victor Nguyen
(74) Attorney, Agent, or Firm—Garvey, Smith, Nehrbass & Doody, L.L.C.; Gregory C. Smith

(57) ABSTRACT

An apparatus for manipulating the rectosigmoid during surgery, to move the rectosigmoid to a pre-determined position, which includes a cannula portin, having a rounded and flexible tip, an inflatable balloon surrounding at least a portion of the cannula; the balloon inflatable with water, gas, or dye; a cone at a first end of the cannula for sealing around the opening of the anus; a stylet insertable in the cannula opening to provide partial rigidity to the cannula; and a syringe lock for introducing the fluid into the balloon, so as to provide a soft yet somewhat rigid device for allowing gentle manipulation of the recto-sigmoid during surgical procedures.

The method performed with the apparatus of the present invention would include the steps of providing a cannula of a certain length, around 20 cm–30 cm; providing an inflatable balloon around at least a portion of the cannula; providing a cone end to at least a first end of the cannula; inserting a hook stylet into the cannula opening to provide some rigidity to the cannula; inserting the second end of the cannula upon which the balloon surrounds into the rectum to a distance of around 10 to 20 cm balloon length; sealing the cone end to the outer surface of the anal opening; inserting a fluid into the balloon to inflate the balloon to around 3 cm–5 cm; moving the outer end of the stylet extending from the cannula in a first direction so that the second end of the cannula is moved in the opposite direction and manipulates the rectosigmoid in that direction.

8 Claims, 3 Drawing Sheets

RECTOSIGMOID MANIPULATOR APPARATUS

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to medical devices. More particularly, the method and apparatus of the present invention relates to an apparatus for insertion into the rectum for manipulating the rectosigmoid to facilitate access to other anatomical structures during surgical procedures.

2. General Background of the Invention

During the course of some surgical procedures, more specifically, minimal invasive surgery, it is at times necessary to be able to gently move the rectosigmoid out of position so as to avoid damage to the structure and to facilitate access to other anatomical locations needed during the procedure. Laparoscopy is commonly used to perform hysterectomies, vaginal vault suspensions using the uterosacral ligaments, also by attachment of the vagina to the hollow of the sacrum, uterine suspensions utilzing the uterosacral ligaments and other surgeries in the gynecological and colo-rectal arena. Previously, to manipulate the rectum, the surgeon would utilize a sponge stick, well lubricated, that was placed in the rectum and pushed up, usually to about 10 cm or to the peritoneal reflection. Another instrument which was utilized was an EES sizer, which was very heavy and again difficult to utilize in laparoscopy.

Other devices which may be related to this procedure are discussed in the patents which are included in the information disclosure statement submitted herewith.

BRIEF SUMMARY OF THE INVENTION

The method and apparatus of the present invention solves the problems in the art in a simple and straightforward manner. What is provided is an apparatus for manipulating the rectosigmoid during surgery, to move the rectosigmoid to a pre-determined position, which includes a cannula portion, having a rounded and flexible tip, an inflatable balloon surrounding at least a portion of the cannula; the balloon inflatable with water, gas, or dye; a cone at a first end of the cannula for sealing around the opening of the anus; a stylet insertable in the cannula opening to provide partial rigidity to the cannula; and a syringe lock for introducing the fluid into the balloon, so as to provide a soft yet somewhat rigid device for allowing gentle manipulation of the rectosigmoid during surgical procedures.

The method performed with the apparatus of the present invention would include the steps of providing a cannula of a certain length, around 20 cm–30 cm; providing an inflatable balloon around at least a portion of the cannula; providing a cone end to at least a first end of the cannula; inserting a hook stylet into the cannula opening to provide some rigidity to the cannula; inserting the second end of the cannula upon which the balloon surrounds into the rectum to a distance of around 10 to 20 cm balloon length; sealing the cone end to the outer surface of the anal opening; inserting a fluid into the balloon to inflate the balloon to around 3 cm; moving the outer end of the stylet extending from the cannula in a first direction so that the second end of the cannula is moved in the opposite direction and manipulates the rectosigmoid in that direction.

Therefore, it is a principal object of the present invention to provide a concise method and apparatus for gently manipulating the rectosigmoid during surgery which is easy to manipulate and efficient in its use;

It is a further object of the present invention to provide an apparatus which allows a surgeon to gently manipulate the rectosigmoid during surgery as to be able, for example, to attach the vagina to the concave of the sacrum, or to more readily locate lesions such as endometriosis;

It is a further object of the present invention to provide an apparatus which allows a physician to avoid injuring the rectum when doing complicated rectocele repairs.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 2 FIG. 1 illustrates an overall view of the apparatus of the present invention inserted within the rectum with the balloon portion inflated.

DETAILED DESCRIPTION OF THE INVENTION

Figure 1:
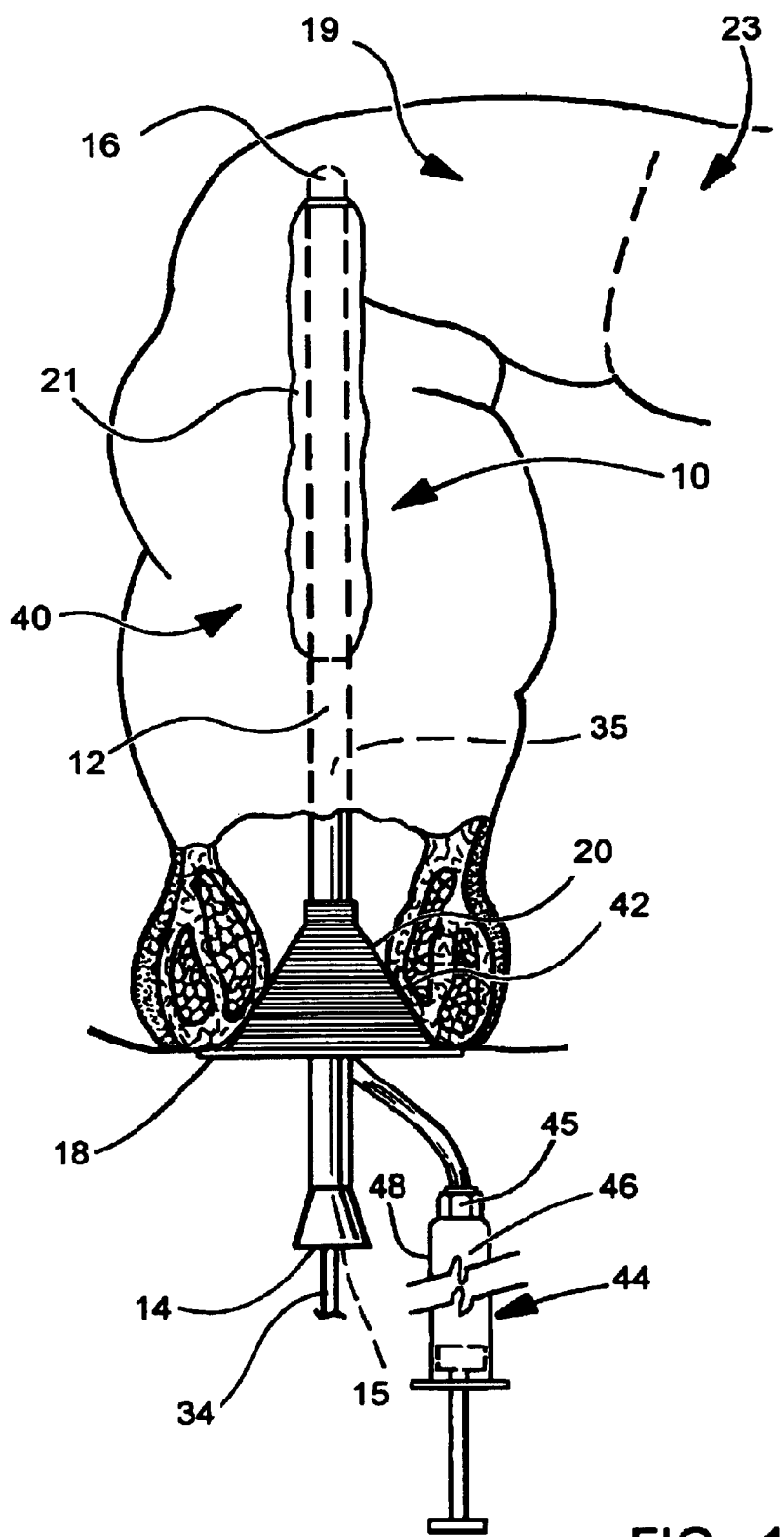
FIG. 1 illustrates an overall view of the apparatus of the present invention inserted within the rectum with the balloon portion uninflated.
Figure 2:
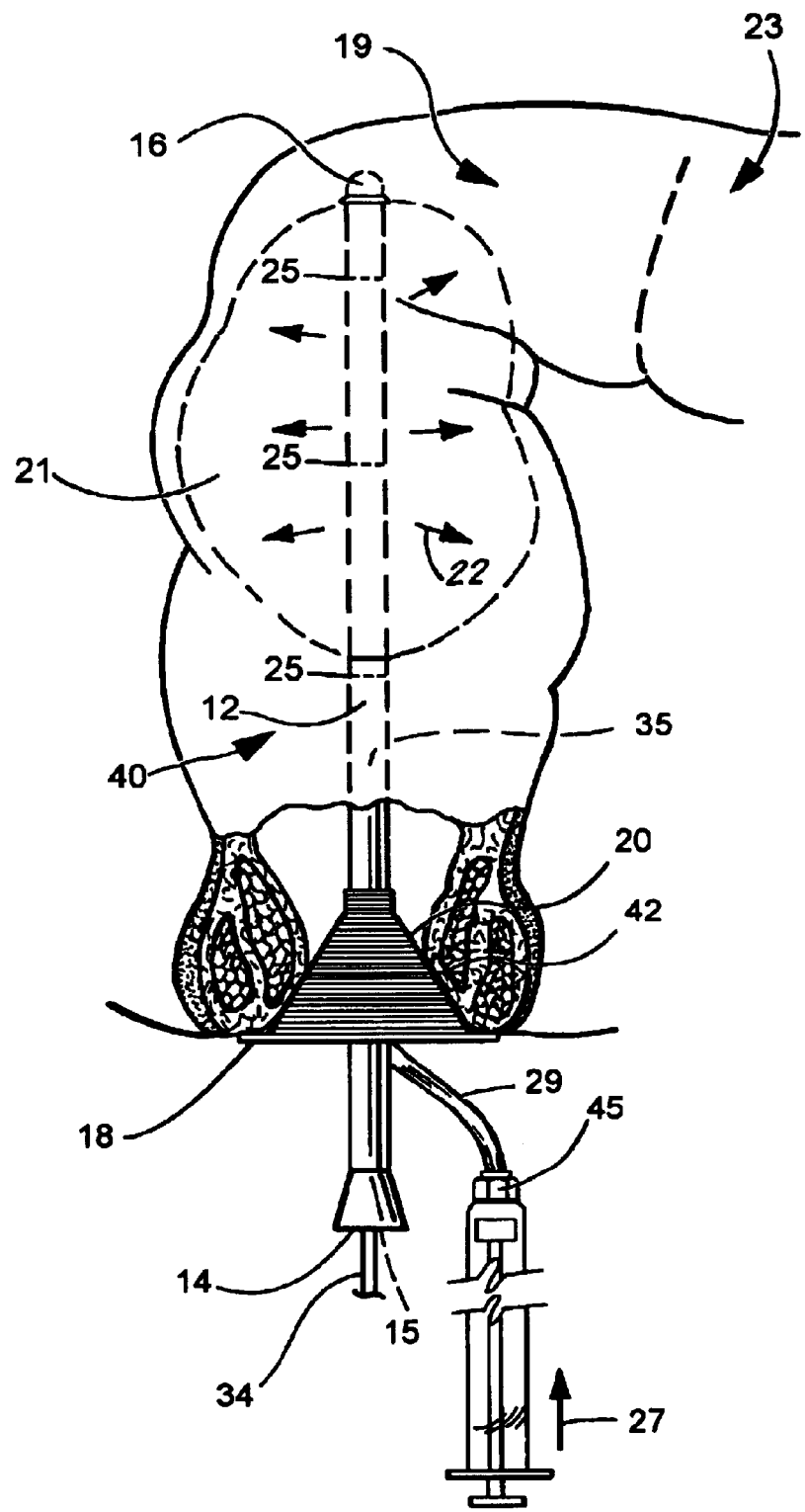
Figure 3:
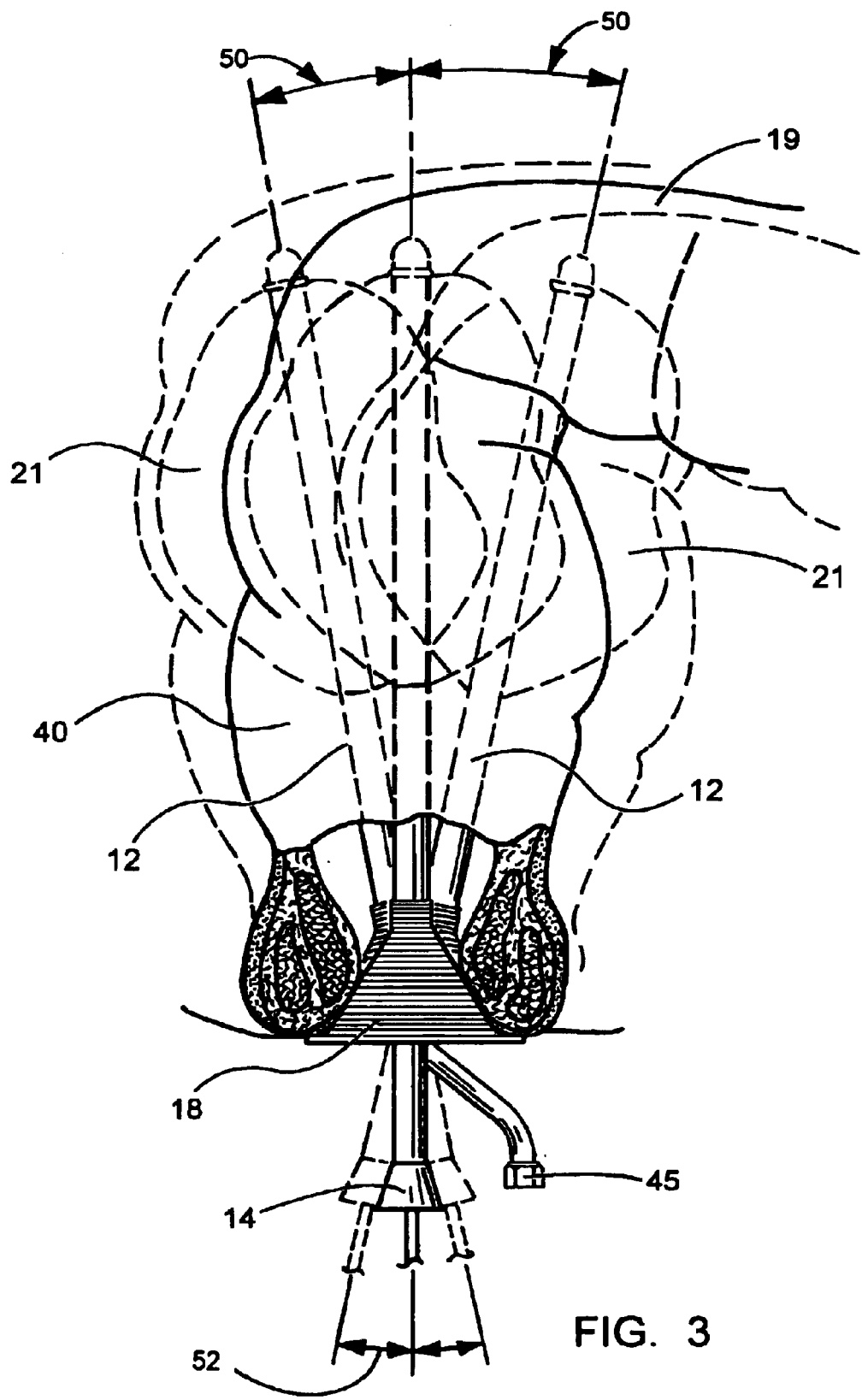
FIG. 3 illustrates an overall view of the preferred embodiment of the apparatus of the present invention inserted into the rectum and manipulating the rectosigmoid.

FIGS. 1–3 illustrate the preferred embodiment of the apparatus and method of the present invention with the apparatus being identified by the numeral 10. As illustrated in full view in FIG. 1, apparatus 10 includes an elongated cannula portion 12 of a predetermined length in the neighborhood of 20 cm–30 cm, having a first open end 14, with an opening 15, and a second closed rounded end 16. As illustrated, cannula 10 further comprises a cone member 18 positioned at a first end 14 of cannula 10, which includes a flat shoulder member 20 which will be utilized in a function to be described further. There is also noted an inflatable balloon portion 21, at the second end 16, the function also which will be identified later.

As seen in FIG. 1, the cannula 10 has been inserted into the rectum 40 of a person, to a point where cannula 10 occupies the entire rectosigmoid portion 19 of the intestine 23. At that point, the shoulder 20 of cone member 18 is making contact with the rectal opening wall 42 and will be sealed there against via taping ore the like. The balloon portion 21 is shown in the deflated state, as illustrated. Further, along the length of cannula 12 there could be a plurality of graduations 25, which represent particular distances along its length in order to provide the depth that the cannula 10 is being inserted into the rectum 40.

As further seen in FIGS. 1 and 2, there is illustrated a stylet member 34, preferably a hook stylet, which has been positioned within the interior space 35 of cannula 10. The hook stylet 34 would be inserted into the cannula 10 in order to provide some rigidity to the cannula 10 during use, although the cannula must remain somewhat flexible to undertake its gentle manipulation task. There would be further provided, as seen in the figures, a syringe 44 which may be integral or secured to the cannula at fixture 45, so that air or a fluid such as water, gel, or other non-toxic, benign fluid 46 within syringe barrel 48 could be inserted to inflate the balloon via line 29 through cannula 12. Preferably the balloon would be inserted to around 3 cm in diameter.

As seen in FIG. 2, the balloon is being inflated (arrows 22)by introducing the fluid (arrow 27) from the syringe 44. The cannula 10, housing the stylet 34 would be ready for use. As seen in FIG. 3, the second end of the stylet 34 would be extending from the opening in the cannula 10 and would be the means by which the cannula 10 would be manipulated within the rectum to manipulate the rectosigmoid 19. Movement of the end of the stylet 34 in a certain direction (arrow 50) would impart movement of the second end of the cannula 10 with the balloon 21 in the opposite direction. (arrow 52). This movement of the rectosigmoid 19 in this manner would define a gentle means for moving the rectosigmoid so the surgeon would have greater access to other anatomical structures and be able to perform difficult surgeries without the rectosigmoid being in harms way.

In construction, the cannula 10 would be preferably constructed of a rubber or latex free material. The length of the cannula would be around 20 cm–30 cm, but the cannula balloon length could vary between 5 cm and 20 cm, depending on its particular use.

| | |
|---|---|
| apparatus | 10 |
| cannula portion | 12 |
| first open end | 14 |
| opening | 15 |
| second closed end | 16 |
| cone member | 18 |
| rectosigmoid | 19 |
| shoulder member | 20 |
| balloon portion | 21 |
| arrows | 22 |
| intestine | 23 |
| graduations | 25 |
| arrow | 27 |
| line | 29 |
| stylet member | 34 |
| interior space | 35 |
| rectum | 40 |
| rectal opening wall | 42 |
| syringe | 44 |
| fixture | 45 |
| fluid | 46 |
| syringe barrel | 48 |
| arrow | 50 |
| arrow | 52 |

The foregoing embodiments are presented by way of example only; the scope of the present invention is to be limited only by the following claims.

What is claimed is:

1. An apparatus for manipulating anatomical structures, including the rectosigmoid, comprising:
   a. a cannula of a predetermined length, having a hollow interior, an open first and a closed second end, the second end insertable a distance into the rectum, wherein the cannula further comprises graduations at 20 cm–15 cm; 10 cm; 7.5 cm; 5 cm and 2.5 cm along its wall between the cone portion and the balloon portion;
   b. means on the first end for sealing the first end of the cannula against the rectal opening;
   c. a stylet insertable into the hollow interior of the cannula;
   d. a balloon surrounding a portion of the exterior of the cannula terminating at the second end of the cannula;
   e. a fluid injectable into the balloon for inflating the balloon so that the apparatus can be gently manipulated against the anatomical structure, including the rectosigmoid, to move the structure during surgery or examinations.

2. The apparatus in claim 1, wherein the inflatable balloon is inflated with air, water, or other benign fluid.

3. The apparatus in claim 2, wherein the sylet insertable within the hollow of the cannula comprises a hook stylet with its second end extending from the first opening of the cannula.

4. The apparatus in claim 1, wherein the means on the first end of the cannula for sealing the first end of the cannula against the rectal wall comprises a cone member sealable against the exterior opening of the rectum.

5. The apparatus in claim 1, wherein the first end of the cannula is closed and rounded for ease of insertion into the rectum.

6. The apparatus in claim 1, wherein the first end of the cannula is adapted with a syringe for injecting the fluid into the balloon.

7. An apparatus for manipulating a rectosigmoid during surgery, comprising:
   a. a cannula of a predetermined length, having a hollow interior, a first open and a closed second end, the second end insertable a distance into the rectum, wherein the cannula further comprises graduations at 20 cm–15 cm; 10 cm; 7.5 cm; 5 cm and 2.5 cm along its wall between the cone portion and the balloon portion;
   b. a balloon surrounding a portion of the exterior of the cannula terminating at the second end of the cannula;
   c. means on the first end for sealing the first end of the cannula against the rectal opening;
   d. a stylet insertable into the hollow interior of the cannula, the stylet having a second end extending from the first end of the cannula;
   d. a fluid injectable into the balloon for inflating the balloon so that the stylet can be used to move the second end of the cannula supporting the inflated balloon to gently manipulate the rectosigmoid, without causing injury to the rectosigmoid.

8. A method of manipulating the rectosigmoid during surgical procedures, comprising the following steps:
   a. providing a cannula of a certain length;
   b. providing an inflatable balloon around at least a portion of the cannula;
   c. providing a cone end to at least a first end of the cannula;
   d. inserting a hook stylet into the cannula opening to provide some rigidity to the cannula;
   e. inserting the second end of the cannula upon which the balloon surrounds into the rectum to a distance of around 10 to 20 cm balloon length;
   f. sealing the cone end to the outer surface of the anal opening;
   g. inserting a fluid into the balloon to inflate the balloon to around 3 cm–5 cm; moving the outer end of the stylet extending from the cannula in a first direction so that the second end of the cannula is moved in the opposite direction and manipulates the rectosigmoid in that direction.

* * * * *